United States Patent [19]

Rampersad et al.

[11] Patent Number: 5,830,712
[45] Date of Patent: Nov. 3, 1998

[54] SELECTIVE TEMPLATE DELETION METHOD

[75] Inventors: Vikarna Rampersad, North York; Roman Zastawny, Etobicoke; Rajender Kamboj, Mississauga, all of Canada

[73] Assignee: Allelix Biopharmaceuticals Inc., Mississauga, Canada

[21] Appl. No.: 597,249

[22] Filed: Feb. 6, 1996

[51] Int. Cl.$^6$ .............................. C12P 19/34; C12Q 1/68; C07H 21/02; C07H 21/04
[52] U.S. Cl. ......................... 435/91.1; 435/6; 435/912; 536/27.3; 536/24.31; 536/24.32; 536/24.33; 536/24.5; 536/22.1; 536/23.1
[58] Field of Search ............................ 435/6, 91.1, 91.2; 536/24.3, 24.31, 24.32, 24.33, 24.5, 22.1, 23.1

[56] References Cited

FOREIGN PATENT DOCUMENTS

WO 93/10267  5/1993  WIPO .

OTHER PUBLICATIONS

Dagle et al, "Targeted degradation of mRNA in *Xenopus oocytes* and embryos directed by modified oligonucleotides: studies of An2 and cyclin in embryogenesis", Nucleic Acids Res. 18(16):4751–4757, 1990.

Seyama et al, "A novel blocker–PCR method for detection of rare mutant alleles in th presence of an excess amount of normal DNA", Nucleic Acids Res. 20(10):2493–2496, 1992.

Buchman et al, "Selective RNA amplification: A novel method using dUMP containing primers and uracil DNA glycosylase", PCR Method and Applications 3(1): 28–31, 1993.

*Primary Examiner*—W. Gary Jones
*Assistant Examiner*—Jeffrey Fredman
*Attorney, Agent, or Firm*—Nikaido Marmelstein Murray & Oram LLP

[57] ABSTRACT

A novel method for inactivating undesirable members in a nucleic acid sample which comprises undesirable and desirable members of a nucleic acid family. The method includes the step of adding a blocker to the sample which selectively associates with the undesirable members such that they are unable to participate in any further processing of the sample. The method advantageously provides a means whereby desirable members of the nucleic acid family can be processed, i.e. identified, amplified and/or isolated, without interference from undesirable sequence-related members.

3 Claims, 1 Drawing Sheet

SELECTIVE TEMPLATE DELETION METHOD

FIELD OF THE INVENTION

This invention relates generally to the field of recombinant DNA technology. In particular, the present invention relates to a method which allows for selective template deletion from a nucleic acid sample.

BACKGROUND TO THE INVENTION

Many proteins belong to multi-gene families. Categorization of proteins into a particular gene family is usually based on the existence of one or more highly conserved regions. Methods for cloning members of a multi-gene family have been developed and generally rely upon knowledge of the conserved regions characteristic of the gene family.

The polymerase chain reaction (PCR) represents a well-known method for cloning members of multi-gene families, and in particular novel members of a given gene family. This method employs degenerate oligonucleotide primers derived from conserved regions of known members of the gene family under PCR conditions to amplify genes, or portions of genes, comprising the conserved regions. Theoretically, this reaction enables amplification of all genes comprising the conserved targetted sequence in a particular tissue source, i.e. all members of a given gene family. In practice, however, this is rarely the case due to the fact that PCR conditions which give optimal amplification of each member of a gene family are difficult to achieve. For example, conditions which are too stringent result in amplification of known family members, which are generally present in abundance, since the primer sequences are biased towards these members, while conditions which are not stringent enough result in the amplification of non-specific sequences.

In order to clone effectively novel or less abundant members of a particular gene family, an efficient means of deleting known or abundant members from the sample prior to conducting the cloning exercise would be desirable. In this way, the cloning method would target only desired members of a gene family and interference by undesired clones, including known structurally similar members of the family or unrelated clones, would be reduced.

SUMMARY OF THE INVENTION

It is an object of the present invention to provide a nucleic acid sample which allows for the preferential cloning of desirable nucleic acids therefrom while minimizing the cloning of undesirable clones. It is also an object of the present invention to provide a method of preparing such a nucleic acid sample.

Accordingly, in one aspect of the present invention there is provided a nucleic acid sample in which undesirable nucleic acids of a nucleic acid family are substantially inactivated.

In another aspect of the present invention, there is provided a method of preparing a nucleic acid sample, which comprises undesirable and desirable nucleic acids of a nucleic acid family, wherein said undesirable nucleic acids are substantially inactivated, said method comprising the step of:

adding to said sample a blocker capable of selectively associating with said undesirable nucleic acids in said sample These and other aspects of the present invention will be described by reference to the accompanying drawing, in which:

BRIEF REFERENCE TO THE DRAWING

FIG. 1 represents the results of an electrophoretic gel analysis of 3 nucleic acid samples prepared using the method of the present invention.

DETAILED DESCRIPTION OF THE INVENTION AND PREFERRED EMBODIMENTS

Figure 1:
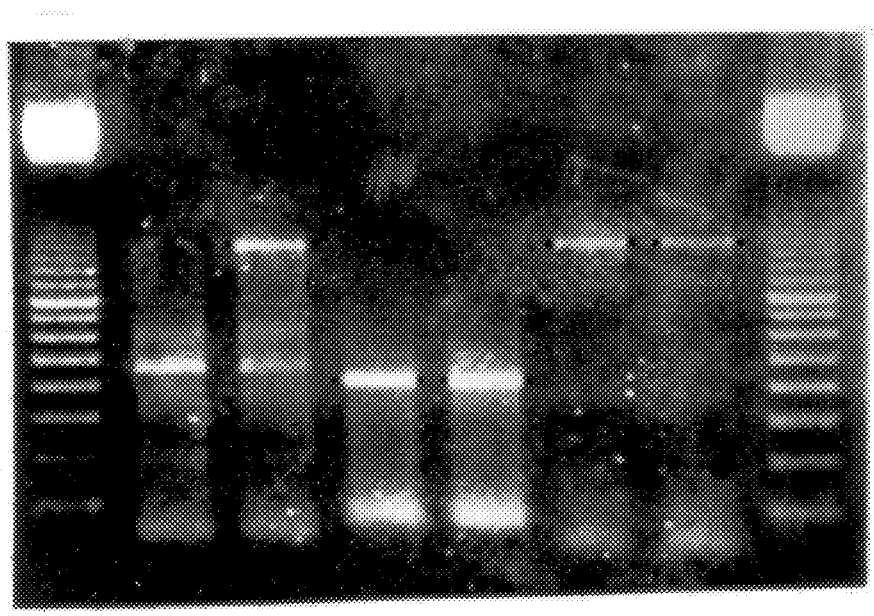

The present invention provides nucleic acid samples in which undesirable nucleic acids of a nucleic acid family are substantially inactivated. A method for preparing such a nucleic acid sample is also provided including the step of adding a blocker to said sample which selectively associates with the undesirable nucleic acids in the sample thereby preventing such nucleic acids from participating in any further processing of the sample. This method advantageously allows for the selective inactivation of nucleic acids that are intimately related to desired nucleic acids in a given sample, the determination of which can be masked by the presence of the undesired nucleic acids.

The term "undesirable nucleic acids" is used herein to denote nucleic acids in a sample that interfere with the use of the sample. Undesirable nucleic acids may include known or abundant members of a nucleic acid family that block the study, isolation or processing of desired novel or less abundant members of the same family. The term "desirable nucleic acids", thus, is used herein to denote nucleic acids within a sample, the identification and further processing of which is desired. Desirable nucleic acids include, for example, novel members of a given nucleic acid family, or members of a nucleic acid family which are less abundant in a sample.

The term "nucleic acid family" refers to a group of nucleic acid molecules which have in common at least one highly conserved region. As will be appreciated, a "conserved region" is a location within each member of the family which exhibits significant sequence homology. The conserved region may comprise as few as 12 homologous nucleotides, or may comprise a much larger region of homology. A multi-gene family is an example of a nucleic acid family in accordance with the present invention. Nucleic acid families may also, however, include as members partial sequences that do not encode an entire protein. The term "nucleic acid sample" is used herein to refer to samples of mRNA and samples of DNA, including either genomic or cDNA.

The term "inactivated" is used herein with respect to those nucleic acids which are prevented from interfering with the analysis and further processing of desired nucleic acids in a nucleic acid sample. As will be appreciated, due to one or any combination of factors inherent in experimental protocol, the term "substantially" is used to indicate that the inactivation of undesired nucleic acids may not necessarily be complete, i.e. 100%.

In order to inactivate undesirable nucleic acids from a nucleic acid sample, the present method comprises the step of adding to the sample a blocker which selectively associates with targetted undesirable nucleic acids. The blocker may be any chemical entity capable of associating with nucleic acids, in a covalent or non-covalent manner, provided that the association is selective in nature, i.e. is restricted to the undesired nucleic acid.

In accordance with one embodiment of the present invention, undesired nucleic acids of a given family can be inactivated using an oligonucleotide blocker. To be selective, the blocker must comprise a sequence which is complementary to a unique region of the undesired nucleic acid. The term "unique region" is used to refer to a sequence in the undesired nucleic acid which occurs at a site not known to be conserved in other members of the nucleic acid family. In this way, the blocker will hybridize only to the target undesired nucleic acid and not to all members of the nucleic acid family. To further encourage selective hybridization of the blocker to the targetted nucleic acid, the blocker is introduced into the nucleic acid sample under stringent hybridization conditions.

The nature of the oligonucleotide blocker is not particularly restricted, providing that it comprises a sequence that is complementary to a unique region within the targetted undesired nucleic acid so as to ensure hybridization of the blocker to the target under stringent conditions. As will be appreciated, the unique region chosen to block undesired nucleic acids must lie between any conserved regions which may later be chosen for priming in a subsequent amplification of step of desired nucleic acids to ensure that undesired nucleic acids are not also amplified. With respect to size, the blocker oligonucleotide must be within a range that confers stability in solution and provides inactivation only of the targeted nucleic acid. Thus, suitable blocker oligonucleotides in accordance with the present invention may range in size from about 17 to about 40 base pairs; however, it will be appreciated that oligonucleotide blockers are not restricted to this size range and, thus, blockers outside of this range may also be used.

On addition of oligonucleotide blockers to a nucleic acid sample under suitable hybridization conditions, the blocker will hybridize selectively to any targeted undesired nucleic acid present in the sample. When the nucleic acid sample is a DNA sample, the oligonucleotide blockers form DNA:DNA hybrids with the undesired nucleic acid. In order to achieve inactivation of the DNA:DNA hybrids, the blocker oligonucleotides must be modified at its 3' end to prevent extension by DNA polymerases, such as Taq polymerase, Klenow fragment and reverse transcriptase, that may be added in subsequent processing steps. The 5' end of the blocker may also be modified to prevent degradation, for example, by 5' to 3' exonuclease activity exhibited by DNA polymerases. Any modification to the terminal nucleotides of the blockers that would function to retard 3' extension and 5' degradation is appropriate to allow the blocker to effectively inactivate the undesirable nucleic acid. Examples of such modifications include addition of an amine, phosphate, acridine or cholesterol group to a terminal nucleotide. Terminal phosphorothioate nucleotide bases are also effective modifications.

When the nucleic acid sample is an mRNA sample, on the addition of oligonucleotide blockers, DNA:RNA hybrids form in the sample. The oligonucleotide blockers may be modified as described above for use with samples of DNA, or the blockers can be used in unmodified form. If the blockers are used in unmodified form, inactivation of undesired RNA clones is achieved by cleavage with enzymes that selectively recognize the DNA:RNA hybrids which form on addition of the blocker to the nucleic acid sample. For example, the sample can be treated with the endoribonuclease, Ribonuclease H (RNase H) which selectively recognizes DNA:RNA hybrids and cleaves the phosphodiester bonds of the RNA. RNase H does not degrade single-stranded or double-stranded DNA or RNA, and thus, this treatment does not eliminate or effect any other species within the mRNA sample.

Any number of different oligonucleotide blockers can be added to a nucleic acid sample for the purpose of inactivating multiple undesirable nucleic acids of a given nucleic acid family. This is useful when a nucleic acid family includes a number of known members and additional members of the family are sought. Oligonucleotide blockers specific for the known members can be added to a nucleic acid sample to mask the known members so that any unknown members that may exist can be more easily identified.

On inactivating the undesirable nucleic acids in a nucleic acid sample as outlined above, the sample comprises only desired nucleic acids of a given family, and thus can be further processed to achieve its contemplated end use, e.g. cDNA library synthesis or isolation of novel clones. A further processing step commonly used in the case of rare or less abundant clones is amplification. As used herein, the term "amplification" is meant to encompass any means by which the concentration of a given nucleic acid can be increased in a sample. Commonly used methods to amplify nucleic acids include the well-established Polymerase Chain Reaction (PCR), and any modified versions thereof. In order to use this methodology to amplify a sample of mRNA, the sample must first be reverse transcribed to form a corresponding sample of cDNA using well-established protocols.

As set out above, one contemplated use for nucleic acid samples prepared in accordance with the invention, i.e. samples in which undesired nucleic acids of a given nucleic acid family are inactivated, is the efficient cloning of novel members of a multi-gene family. By providing a nucleic acid sample from which known members of the gene family have been selectively inactivated, novel members of the family, which are often less abundant than their known counterparts, can selectively be amplified, identified and isolated without undue interference. In this regard, it is believed that a protocol according to the present method will provide a valuable tool in novel gene discovery.

Another use of the present method lies in the preparation of specific cDNA libraries, i.e. cDNA libraries rich with respect to certain cDNAs . Thus, cDNA libraries rich in novel cDNAs can be prepared by using the present method to inactivate known members of a nucleic acid family and allow isolation of unknown members of the family. Moreover, cDNA libraries rich with respect to specific known cDNAs can also be prepared by selectively inactivating undesirable known members to enable isolation of the desired cDNAs.

The present invention is described in further detail by reference to the following specific example which is not to be construed as limiting.

EXAMPLE 1

Total rat hypothalamus RNA (15 μg) was incubated with 25 pmoles of a rat NPY Y1 specific 3' modified oligonucleotide blocker as follows:
5'-GACCCAGACACTGGACCTGTACTTACTGTCCC-TGATTTG-C3-amine-3'(SEQ ID NO: 1)

The reaction also contained 50 mM KCl, 10 mM Tris-HCl pH 8.3, 5.0 mM $MgCl_2$, 50 units RNase inhibitor and 2 units RNase H, in a total reaction volume of 20 μl. The reaction was incubated at 37° C. After 30 minutes, the reaction was diluted with 30 μl of DEPC water and extracted with 1 volume of Phenol:Chloroform:Isoamyl alcohol (25:24:1) followed by a single extraction with one volume of chloroform. The reaction was subsequently precipitated with 0.1 volume of 3M sodium acetate, pH 5.2, and 2.5 volumes of ethanol. The pelleted RNA was washed with 70% ethanol, air dried and resuspended in 30 μl DEPC water (~0.5 μg/l). A control sample in which the specific oligonucleotide blocker and RNase H were substituted with DEPC water was run in parallel with the above sample. Aliquots (2μl) of both treated and control RNA samples (plus or minus oligonucleotide blocker and RNase H) were used as templates in reverse transcription-PCR reactions using the GeneAmp RNA PCR Kit (Perkin Elmer). RT reactions, in a total volume of 20 μL, contained 50 mM KCl, 10 mM Tris-HCl pH 8.3, 5.0 mM $MgCl_2$, 1mM of each deoxyribonucleoside triphosphate, 50 units of RNase Inhibitor, 125 units MuLV Reverse Transcriptase. In a first set of RT reactions, 25 pmoles of a 'downstream' PCR oligonucleotide primer complementary to the rat NPY Y1 cDNA sequence was used. In a second set of RT reactions, 25 pmoles of a 'downstream' PCR oligonucleotide primer complementary to the rat NPY Y2 cDNA sequence was used, and in a third set of RT reactions, 25 pmoles of a 'downstream' PCR oligonucleotide primer complementary to the rat PP1 cDNA sequence. Accordingly, a total of 6 RT reactions were performed.

Each RT reaction was conducted as follows: 30 minutes at 42° C.; 99° C. for 5 minutes and 4° C. for 5 minutes. In the subsequent PCR reactions, components required for PCR were added directly to the RT reactions which brought the final volume up to 100 μl. The PCR reactions contained 50 mM KCl, 10 mM Tris-HCl pH 8.3, 2.0 mM $MgCl_2$, 0.5mM of each deoxyribonucleoside triphosphate, 2.5 units of Taq polymerase and 25 pmoles 1 of 3 specific 'downstream' and 'upstream' PCR oligonucleotide primers complementary to either the rat NPY Y1, Y2 or PP1 cDNA sequence. The PCR reaction was conducted as follows: 94° C. for 30 seconds, 55° C. for 30 seconds and 72° C. for 60 seconds for a total of 30 cycles.

An aliquot of each of the PCR reactions was electrophoresed on a 2% agarose gel. FIG. 1 illustrates the results of the electrophoretic analysis. As can be seen, the Y1 message was specifically depleted from the RNA sample that included the oligonucleotide blocker (lane 1) in contrast to the control sample to which no blocker was added (lane 2). As can be seen by reference to lanes 3–4 and lanes 5–6, the elimination of Y1 RNA was specific and did not affect the level of mRNA of 2 related but different NPY family members - Y2 (compare lane 3 and 4) and PP1 (compare lane 5 and 6). Hence, the above protocol can be used to selectively deplete specific mRNA species within a pool of RNA.

An unmodified oligonucleotide blocker can be used in the above-identified protocol. Alternatively, it may be preferable to physically remove the oligonucleotide blocker prior to further processing of the RNA sample (e.g. cDNA library synthesis or RT-PCR). The above protocol could readily be modified to accomodate either of these alternatives. For example, following the RNase H treatment of the RNA pool, the unmodified oligonucleotide blocker could be physically removed from the sample by column chromatography or by using biotin/streptavidin-magnetic bead technology. Once the blocker oligonucleotide is physically removed from the sample, the RNA pool can then be further treated as described above.

EXAMPLE 2

Two degenerate oligonucleotides based on sequences complementary to specific regions conserved within all members of a multigene family are used as primers in a polymerase chain reaction to amplify all possible members of a multigene family present in a choosen pool of cDNA. In addition, the reaction includes specific oligonucleotide blockers based on sequences specific for one or more particular family members within the multigene family which are to be inactivated such that their amplification is prevented. The oligonucleotide blocker(s) are situated between the 'downstream' and 'upstream' degenerate PCR primers and are modified at their 3' and 5' ends.

The PCR reaction contains in a total volume of 50 μl, 50 mM KCl, 10 mM Tris-HCl pH 8.3, 2 mM MgCl2, 0.2 mM dNTPs, 25 pmoles of each specific oligonucleotide blocker, 25 pmoles each of a 'downstream' and 'upstream' degenerate PCR primer, 50–100 ng of cDNA and 2.5 units AmpliTaq DNA polymerase. The PCR reaction is conducted as follows: 94° C. for 2 minutes, 65° C. for 30 seconds, 52° C. for 30 seconds and 72° C. for 1 minute for 25 cycles. The initial annealing at 65° C. prior to lowering the temperature to 52° C. allows the oligonucleotide blocker(s) to hybridize to the template cDNA before the PCR primers anneal to the template cDNA causing its amplification. It is important to note, with respect to the PCR conditions to be used, that the exact annealing temperatures used depend on the length and composition of the oligonucleotide blockers and PCR primers used. The oligonucleotide blocker(s), thus, are designed such that their Tm (temperature at which 50% of the oligonucleotide blocker:cDNA complex dissociates) is much higher than the Tm of the PCR primers. In this regard, the Tm of the oligonucleotide blockers can be increased by incorporating acridine groups within the blocker to stabilize the blocker:cDNA complexes formed. Under conditions, all members of the multigene family within the cDNA pool would be efficiently amplified except for the family members inactivated by the oligonucleotide blockers.

We claim:

1. A method of reducing cloning interference by undesirable nucleic acids in a mRNA sample, comprising:

providing a mRNA sample which comprises a nucleic acid family comprising desirable nucleic acids which are to be cloned in a desirable nucleic acids cloning process and undesirable nucleic acids which are capable of interfering in the desirable nucleic acids cloning process;

combining the mRNA sample with a blocker capable of selectively associating with the undesirable nucleic acids and forming a hybrid between the blocker and the undesirable nucleic acids such that the hybrid is incapable of participating in the desirable nucleic acids cloning process; and cleaving the hybrid formed in said combining step.

2. The method of claim 1, wherein the hybrid is cleaved with Ribonuclease H.

3. The method of claim 1, wherein the blocker is an oligonucleotide.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i x ) FEATURE:
( A ) NAME/KEY: modified_base
( B ) LOCATION: 40
( D ) OTHER INFORMATION: /mod_base=OTHER
/ label= C3-AMINE ( x i ) SEQUENCE DESCRIPTION: SEQ ID NO:1:

GACCCAGACA CTGGACCTGT ACTTACTGTC CCTGATTTTG    40